US00PP21536P3

(12) United States Plant Patent
Amrhein et al.

(10) Patent No.: US PP21,536 P3
(45) Date of Patent: Nov. 30, 2010

(54) RASPBERRY PLANT NAMED 'PACIFIC ROYALE'

(50) Latin Name: *Rubus idaeus L.*
Varietal Denomination: Pacific Royale

(75) Inventors: Thomas Amrhein, Watsonville, CA (US); Mario Aguas, Freedom, CA (US)

(73) Assignee: Pacific Berry Breeding, LLC, Salinas, CA (US)

( * ) Notice: Subject to any disclaimer, the term of this patent is extended or adjusted under 35 U.S.C. 154(b) by 0 days.

(21) Appl. No.: 12/384,270

(22) Filed: Apr. 2, 2009

(65) Prior Publication Data

US 2010/0257646 P1 Oct. 7, 2010

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent L Bell
(74) *Attorney, Agent, or Firm*—Jondle & Associates, P.C.

(57) ABSTRACT

'Pacific Royale' is a new raspberry cultivar particularly distinguished by having large, conical fruit, exceptional flavor, firm flesh and resistance to *Phytophthora rubi*, is disclosed.

1 Drawing Sheet

Genus and species: *Rubus idaeus* L.
Variety denomination: 'Pacific Royale'.

BACKGROUND OF THE NEW PLANT

This invention relates to a new and distinct variety of raspberry (*Rubus idaeus* L.) plant named 'Pacific Royale'. 'Pacific Royale' originated as a seedling from a cross between an unknown female raspberry plant (unpatented) and an unknown male raspberry plant (unpatented) in 2003 in Oxnard, Calif.

The new cultivar was first propagated in Watsonville, Calif. in June 2007 and has been asexually reproduced repeatedly by vegetative cuttings and tissue culture in Watsonville, Calif. for two generations. The present invention has been found to retain its distinctive characteristics through successive asexual propagations via vegetative cuttings.

Plant Breeder's Rights for this cultivar have not been applied for prior to the filing of this application. 'Pacific Royale' has not been made publicly available more than one year prior to the filing of this application.

SUMMARY OF THE INVENTION

The following are the most outstanding and distinguishing characteristics of this new cultivar when grown under normal horticultural practices in Watsonville, Calif.

1. Large, conical fruit;
2. Exceptional flavor;
3. Firm flesh; and
4. Resistance to *Phytophthora rubi*

DESCRIPTION OF THE PHOTOGRAPH

This new raspberry plant is illustrated by the accompanying photograph which shows a close-up of the plant's berry from an 8 month-old plant in Watsonville, Calif. The colors shown are as true as can be reasonably obtained by conventional photographic procedures.

DESCRIPTION OF THE NEW CULTIVAR

The following detailed description sets forth the distinctive characteristics of 'Pacific Royale'. The data which define these characteristics were collected from asexual reproductions carried out in Watsonville, Calif. The plant history was taken on 1-and one-half year-old plants in August 2008. The following descriptions relate to plants grown in a field in Watsonville, Calif. Color references are to The R.H.S. Colour Chart of The Royal Horticultural Society of London (R.H.S.), 4$^{th}$ Edition.

DETAILED BOTANICAL DESCRIPTION

Classification:
- *Family.*—Rosaceae.
- *Botanical.*—*Rubus idaeus* L.
- *Common name.*—Raspberry.

Plant:
- *Form and habit.*—Erect growth habit; primocane fruiting; canes grow to about 1.7 m before terminating in an inflorescence.
- *Height* (*measured from crown to apex*).—133 cm.
- *Spread* (*measured from leaf tip to leaf tip*).—41 cm.
- *How propagated.*—Root cuttings.
- *Time to initiate and develop roots.*—70 days.
- *Root description.*—Fibrous.
- *Root diameter.*—0.2 cm to 0.4 cm.

Primocanes:
- *Diameter.*—1.03 cm.
- *Length.*—133 cm.
- *Number of nodes.*—16.
- *Internode length.*—5.1 cm.
- *Number of canes/hill.*—4 to 6.
- *Cane color.*—RHS 146D.
- *Spine.*—Present. Amount per given area: 8.0 cm$^2$. Shape: Acuminate. Length: 0.1 cm. Width: 0.02 cm. Apex descriptor: Acuminate. Spine color: RHS 187B.

Floricanes:

*Diameter.*—11 cm to 14 cm.

*Length.*—83 cm.

*Number of nodes.*—22.

*Internode length.*—6 cm.

*Cane color.*—RHS 178A.

Leaves:

*Arrangement.*—Alternate.

*Terminal leaflet.*—Cordate, lobed.

*Size of terminal leaflet.*—Length: 12 cm. Width: 10.5 cm. Shape of apex: Cuspidate. Shape of base: Cordate. Margin: Doubly-serrate. Texture: Glabrous. Number of serrations/leaf: 106 to 144. Shape of serrations: Doubly-serrate; pointed. Venation pattern: Palmate. Venation color: Upper surface: RHS 146B. Lower surface: RHS 146D. Number of leaflets/leaf: 3 to 5. Glossiness: Not present.

*Primocane Leaves.*—Petiole length: 5.8 cm. Diameter: 0.22 cm. Color: Upper surface: RHS 178A. Lower surface: RHS 145B. Rachis length: 6.2 cm. Diameter: 0.3 cm. Color: Upper surface: RHS 184A. Lower surface: RHS 145B. Stipule: Amount per leaf: 2 per leaf. Length: 1.1 cm. Width: 0.09 cm. Color: RHS 144B. Color: Upper surface: RHS 137A. Lower surface: RHS 191A.

*Terminal leaflet.*—Length: 12 cm. Width: 10.5 cm. Petiolule length: 2.1 cm. Diameter: 0.1 cm. Color: Upper surface: RHS 184A. Lower surface: RHS 145C.

*Distal lateral leaflet.*—Length: 9 cm. Width: 6.5 cm. Petiolule length: 2 cm. Diameter: 0.1 cm. Color: Upper surface: RHS 178A. Lower surface: RHS 145C.

*Basal lateral leaflet.*—Length: 14 cm. Width: 11 cm. Petiolule length: 2.2 cm. Diameter: 0.1 cm. Color: Upper surface: RHS 178A. Lower surface: RHS 145C.

Flowers:

*Bud.*—Shape: Acute. Length: 0.8 cm. Diameter (base): 0.6 cm. Diameter (tip): 0.1 cm. Color: RHS 146C.

*Time of flowering* (50% *of plants at first flower*).—Mid-August on primocanes. Size: Length: 0.7 cm. Diameter: 1.6 cm. Fragrance: None. Color: RHS 155A.

*Peduncle.*—Length: 11 cm to 14 cm. Diameter: 1.6 cm. Color: RHS 144A. Pubescence: Present.

*Petal.*—Number: 5 per flower. Shape: Obtuse. Length: 0.7 cm. Width: 0.32 cm. Apex: Obtuse. Base: Obtuse. Margin descriptor: Entire, with some undulation near apex.

*Petal color* (*both upper and lower surfaces*).—RHS 155A.

*Flowering trusses shape.*—Flattened with rounded edges.

*Sepal.*—Quantity: 5. Length: 0.8 cm. Width: 0.5 cm. Color: RHS 146C. Shape: Acuminate. Apex: Acuminate. Margin descriptors: Entire.

*Pedicel.*—Color: RHS 146C. Length: 1.2 cm. Diameter: 0.14 cm.

Reproductive organs:

*Self fertile.*—Yes.

*Stamens* (*number*).—About 70.

*Filament.*—Length: 0.7 cm. Diameter: 0.1 cm.

*Stamen color.*—RHS 155C.

*Anthers.*—Color (post dehiscence): RHS 199C. Length: 0.1 cm. Diameter: 0.05 cm.

*Pollen color.*—RHS 155A.

*Pollen amount.*—Moderate.

*Style.*—Length: 0.5 cm. Diameter: 0.1 cm. Color: RHS 155D.

*Stigma.*—Length: 0.02 cm. Diameter: 0.01 cm. Color: RHS 8D.

Fruit:

*Predominant shape.*—Conical.

*Average berry weight* (*for primocanes and floricanes*).—4.7 g.

*Berry brix.*—9.54.

*Size.*—Length: 2 cm. Width: 1.7 cm.

*Receptacle.*—Diameter: 1.9 cm. Length: 0.6 cm. Color: RHS 16D.

*Drupelet.*—Diameter: 0.3 cm. Width: 0.4 cm. Number: 96 to 106. Weight: 0.2 g.

*Color of mature fruit.*—External: RHS 46A. Internal: RHS 47A.

*Firmness of skin.*—Very firm.

*Firmness of flesh.*—Very firm.

*Hollow center.*—Yes.

*Number of fruit per node:* 3 to 6.

*Time of ripening* (50% *of plants with first ripe fruit*).—Late-September on primocanes.

*Time of fruiting.*—Floricanes: Spring. Primocanes: Late summer.

*Type of bearing.*—Both on previous year's canes in summer and on current year's canes in autumn.

*Fruit yield.*—1.8 Kg/plant.

*Market use.*—Fresh.

*Keeping quality.*—Excellent.

*Shipping quality.*—Very good.

Resistance to diseases, insects and mites: Resistant to *Phytophthora rubi*, atypical of species.

COMPARISON WITH KNOWN CULTIVARS

'Pacific Royale' differs from the proprietary raspberry plant '401' (unpatented) in that 'Pacific Royale' has brighter fruit color and fewer spines than '401'.

'Pacific Royale' differs from the raspberry plant '431' (unpatented) in that 'Pacific Royale' has larger, firmer fruits than '431'.

'Pacific Royale' differs from the commercial variety 'Caroline' (U.S. Plant Pat. No. 10,412) in that 'Pacific Royale' has larger fruit and a higher fruit yield per plant than 'Caroline'.

The parental lines are no longer available for comparison.

We claim:

1. A new and distinct cultivar of raspberry plant as shown and described herein.

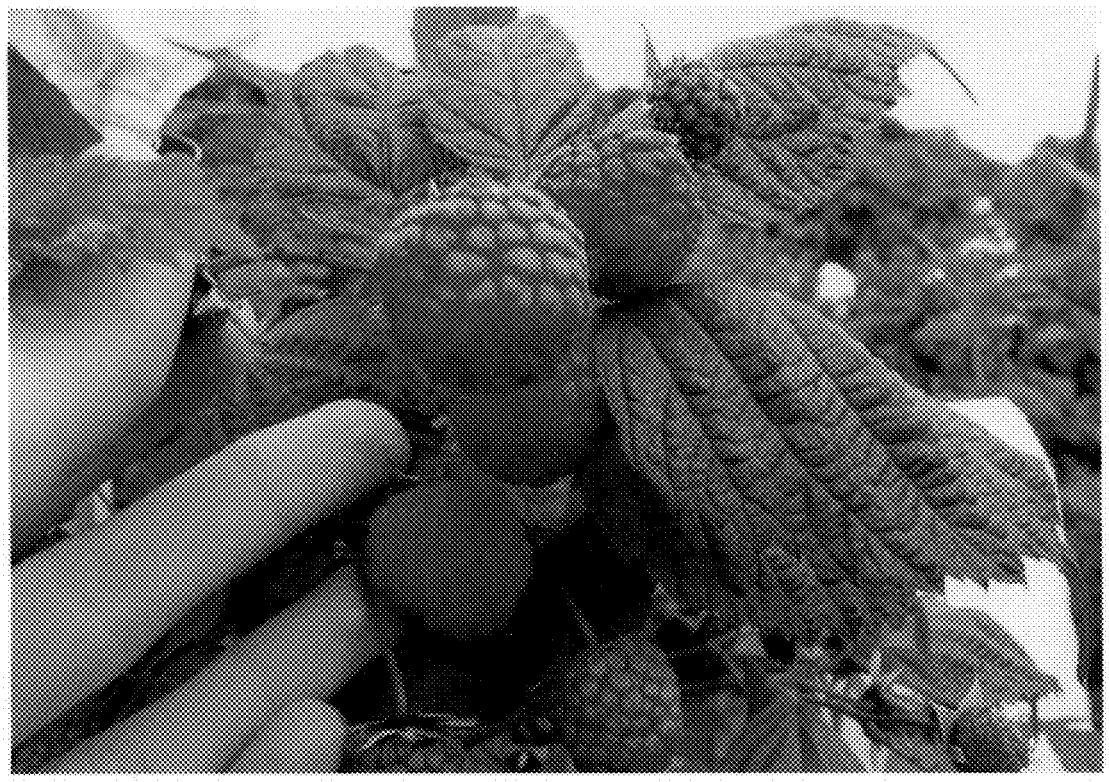

* * * * *